United States Patent
Konradi et al.

(10) Patent No.: US 12,312,572 B2
(45) Date of Patent: *May 27, 2025

(54) DEVICES FOR CULTIVATING CELLS COATED WITH A COPOLYMER OF POLYETHYLENEGLYKOL (METH)ACRYLATE

(71) Applicant: BASF SE, Ludwigshafen am Rhein (DE)

(72) Inventors: Rupert Konradi, Ludwigshafen (DE); Veronique Schwartz, Ludwigshafen (DE); Michael Seufert, Ludwigshafen (DE); Lars David Renner, Dresden (DE); Uwe Freudenberg, Dresden (DE); Carsten Werner, Dresden (DE)

(73) Assignee: FACELLITATE GMBH, Mannheim (DE)

( * ) Notice: Subject to any disclaimer, the term of this patent is extended or adjusted under 35 U.S.C. 154(b) by 504 days.

This patent is subject to a terminal disclaimer.

(21) Appl. No.: 16/627,518

(22) PCT Filed: Jul. 20, 2018

(86) PCT No.: PCT/EP2018/069735
§ 371 (c)(1),
(2) Date: Dec. 30, 2019

(87) PCT Pub. No.: WO2019/025207
PCT Pub. Date: Feb. 7, 2019

(65) Prior Publication Data
US 2020/0148991 A1    May 14, 2020

(30) Foreign Application Priority Data
Aug. 1, 2017 (EP) .................................. 17184267

(51) Int. Cl.
*C12M 1/00* (2006.01)

(52) U.S. Cl.
CPC .................................. *C12M 23/20* (2013.01)

(58) Field of Classification Search
None
See application file for complete search history.

(56) References Cited

U.S. PATENT DOCUMENTS

| 11,150,219 B2* | 10/2021 | Konradi | G01N 29/036 |
| 2011/0312084 A1 | 12/2011 | Delprat et al. | |
| 2015/0010999 A1* | 1/2015 | Caracci | C12M 23/20 |
| | | | 435/396 |
| 2016/0002581 A1 | 1/2016 | Delprat et al. | |
| 2016/0351443 A1* | 12/2016 | George | B32B 15/08 |
| 2018/0056245 A1 | 3/2018 | Konradi et al. | |

FOREIGN PATENT DOCUMENTS

| WO | WO 2013/116432 A1 | 8/2013 |
| WO | WO 2016/166084 A1 | 10/2016 |

OTHER PUBLICATIONS

International Search Report issued Oct. 10, 2018 in PCT/EP2018/069735 filed Jul. 20, 2018.
U.S. Appl. No. 16/322,773, filed Feb. 1, 2019, Rupert Konradi.
International Preliminary Report on Patentability and Written Opinion of the International Searching Authority issued on Feb. 4, 2020 in PCT/EP2018/069735 filed Jul. 20, 2018, 6 pages.

* cited by examiner

*Primary Examiner* — Vera Afremova
(74) *Attorney, Agent, or Firm* — Armstrong Teasdale LLP

(57) ABSTRACT

Device D for cultivating cell cultures C, wherein said device D has a surface O and comprises on its surface O at least one polymer P wherein said polymer P is a copolymer of at least one monomer M and at least one ester E of (meth)acrylic acid and polyethylene oxide, wherein said monomer M is different from ester E and has at least one ethylenically unsaturated double bond.

12 Claims, 2 Drawing Sheets

Figure 1:
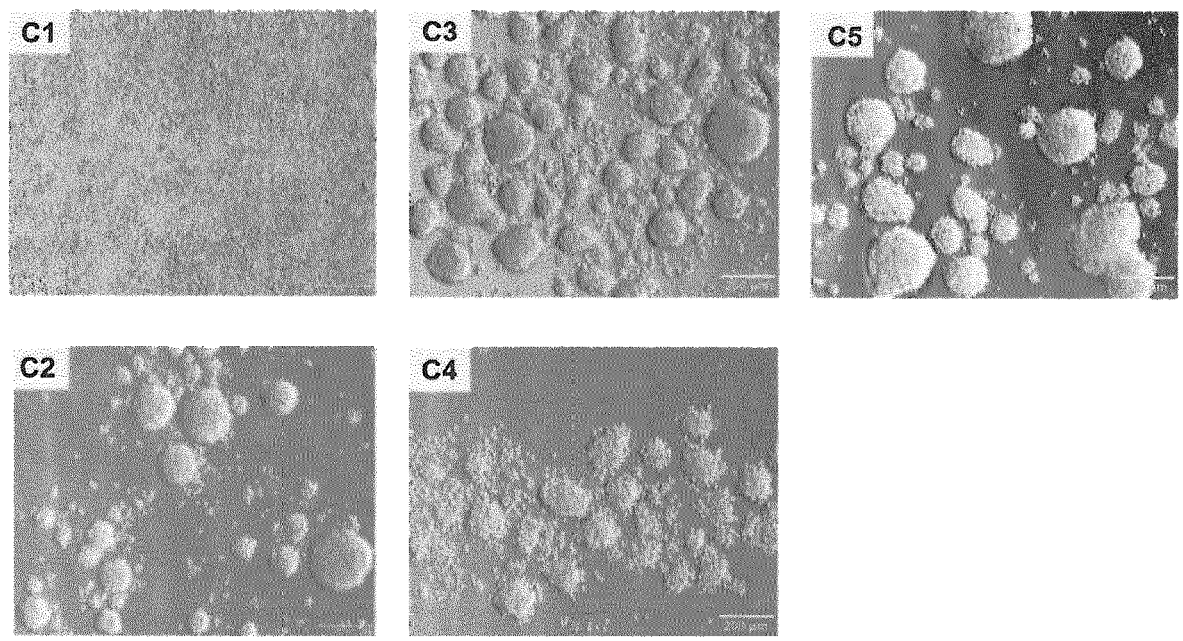

DEVICES FOR CULTIVATING CELLS COATED WITH A COPOLYMER OF POLYETHYLENEGLYKOL (METH)ACRYLATE

The present invention is directed to devices D for cultivating cell cultures C, wherein said device D has a surface O and comprises on its surface O at least one polymer P wherein said polymer P is a copolymer of at least monomer M and at least one ester E of (meth)acrylic acid and polyethylene oxide, wherein said monomer M is different from ester E and has at least one ethylenically unsaturated double bond, wherein polymer P has a surface adsorption SA of at least 200 ng/cm$^2$ on polystyrene, said SA being determined by quartz crystal microbalance. The present invention is further directed to a device D for cultivating cell cultures C, wherein said device D has a surface O and comprises on its surface O at least one polymer P wherein said polymer P is a copolymer of at least one monomer M and at least one ester E of (meth)acrylic acid and polyethylene oxide, wherein said monomer M is different from the ester E and has at least one ethylenically unsaturated double bond. It is more especially directed to devices D comprising at least one polymer P wherein said polymer P is a copolymer of styrene and at least one ester E of (meth)acrylic acid and polyethylene oxide.

Cultivation of cell cultures plays an important role in many technologies.

An important issue with cultivating cells is to provide a suitable environment for the respective cell culture. Some cell types referred to as non-adherent cell cultures grow in a liquid medium and not attached to a surface. Other cell types referred to adherent cell cultures grow attached to a surface such as the bottom of the culture flask.

Cell cultivation in general is well known. There is a need for improved devices for cultivating cells. It was the objective of the present to provide improved devices for cultivating different types of cell cultures.

This objective was achieved by a device D for cultivating cell cultures C, wherein said device D has a surface O and comprises on its surface O at least one polymer P wherein said polymer P is a copolymer of at least monomer M and at least one ester E of (meth)acrylic acid and polyethylene oxide, wherein said monomer M is different from ester E and has at least one ethylenically unsaturated double bond, wherein polymer P has a surface adsorption SA of at least 200 ng/cm$^2$ on the respective surface where polymer P is deposited, said SA being determined by quartz crystal microbalance, e.g. by the method given in the experimental section.

This objective was also achieved by a device D for cultivating cell cultures C, wherein said device D has a surface O and comprises on its surface O at least one polymer P wherein said polymer P is a copolymer of at least one monomer M and at least one ester E of (meth)acrylic acid and polyethylene oxide, wherein said monomer M is different from the ester E and has at least one ethylenically unsaturated double bond.

In one preferred embodiment, said polymer P is a copolymer of styrene and at least one ester E of (meth)acrylic acid and polyethylene oxide.

Devices for cultivating cell cultures are in principle known in the art. Devices D can for example be any device that is suitable for cultivating cells or for handling such cell cultures. In another form devices D can for example be any device that is suitable for cultivating cells including handling such cell cultures.

Examples of devices D include flasks (e.g. round bottom flasks, spinner flasks, Erlenmeyer flasks, retorts, Florence flasks), cell culture dishes, cell culture bottles, cell culture bags, pipette tips, petri dishes, multiwall plates, reactors, especially bioreactors, of all shapes and sizes. Devices D can be lab scale devices, semi industrial size devices or industrial size devices. Typical commercial sizes are for instance 3 L, 50-200 L or 1000-2000 L. Further examples of devices D suitable for handling cell culture containing liquids include tubes, pipettes, syringes. Preferably, the device D is selected from flasks, cell culture dishes, cell culture bottles, cell culture bags, pipette tips, petri dishes, multiwall plates, reactors, tubes, pipettes, syringes.

Devices D have a surface O. Surface O of Devices D can in principle be made of any material on which cell cultures can be grown, be it with the cells being attached to surface O or not.

Preferably, surfaces O are at least partly made of glass, quartz, silicon, metals, metal oxides or organic polymers. In another preferred form, the surface O is at least partly made of organic polymers, such as polyolefines.

Suitable organic polymers for surfaces O include polycarbonate, polystyrene, hydrophilized polystyrene, polyamide, poly(methyl methacrylate), polyesters, polyvinylchloride, polyvinylidene chloride, polymers comprising fluorinated monomers like fluorinated ethylene or propylene, polyolefines (such as polyethylene (like low density polyethylene, ultralow density polyethylene, linear low density polyethylene, high density polyethylene, high molecular weight polyethylene, ultrahigh molecular weight polyethylene), polypropylene, (like oriented polypropylene, biaxially oriented polypropylene), polynorbomene, cyclic olefin polymers (COP) or cyclic olefin copolymers (COC) such as copolymers of ethylene and norbornene). In one embodiment, organic polymers are polyester nonwovens.

Especially preferably, surfaces O of devices D are at least partly made of polyolefines, in particular polystyrene, polyethylene or polypropylene or (partially) fluorinated polyolefines such as fluorinated ethylene propylene. In another form, the surfaces O of devices D are at least partly made of polyolefines, in particular polystyrene, polyethylene, polypropylene, fluorinated polyolefines (such as fluorinated ethylene propylene), or partially fluorinated polyolefines.

In one especially preferred embodiment, surfaces O of devices D are at least partly made of polystyrene.

The term "surfaces O are at least partly made of a material" usually means that at least 50%, preferably at least 80%, and in particular at least 95% of the surface O are made of a material. The surface O of the device D usually refers to that part of the surface which in general comes into contact with the cell cultures C under normal operating conditions.

According to the invention, surface O is usually at least partly coated with at least one polymer P.

Polymer P is preferably a copolymer of at least one monomer M and at least one ester E of (meth)acrylic acid and polyethylene oxide, wherein said monomer M is different from ester E and has at least one ethylenically unsaturated double bond, wherein polymer P has a surface adsorption number SA of at least 100, preferably 200 ng/cm$^2$ on the respective surface where it has been deposited (such as polystyrene), said SA being determined by quartz crystal microbalance, e.g. as described in the experimental section.

The surface adsorption number SA is a parameter that describes the ability of polymers to be adhesively bound to a surface. A high SA indicates that a polymer is strongly bound to a surface. A low SA indicates that a polymer is weakly bound to a surface.

The SA of a polymer is usually determined by quartz crystal microbalance (QCM) according to the procedure given in the experimental section.

Polymer P normally comprises at least one monomer M and ester E in a molar ratio from 0.05 to 50 (e.g. meaning that the molar ratio of monomers M to esters E is 0.05:1 to 50:1). Preferably, the molar ratio of monomers M to ester E in polymer P is 0.2:1 to 15:1, more preferably 0.3:1 to 10:1 and especially preferably 0.5:1 to 4:1. In another form the polymer P comprises at least one monomer M and ester E in a molar ratio from 1:3 to 3:1, preferably from 1:2 to 2:1, and in particular from 1:1.5 to 1.5:1.

Polymer P preferably comprises one monomer M. Polymer P preferably comprises no further monomers beside the monomer M and the ester E. In one preferred embodiment, monomer M is styrene. In this embodiment polymer P thus comprises styrene and at least one ester E of (meth)acrylic acid and polyethylene oxide. In the context of this application, this shall mean that polymer P comprises these monomers in polymerized form.

Polymer P normally comprises styrene and ester E in a molar ratio from 0.05 to 50 (meaning that the molar ratio of styrene to ester E is 0.05:1 to 50:1). In general, for such copolymers of styrene and ester E, the SA is always considered to be at least 200 ng/cm$^2$ and the measurement of the SA is not necessary. Preferably, the molar ratio of styrene to ester E in polymer P is 0.2:1 to 15:1, more preferably 0.3:1 to 10:1 and especially preferably 0.5:1 to 2:1. In another form the polymer P comprises styrene and ester E in a molar ratio from 1:3 to 3:1, preferably from 1:2 to 2:1, and in particular from 1:1.5 to 1.5:1.

In one embodiment, ester E is an ester of acrylic acid and polyethylene oxide.

In one embodiment, ester E is an ester of methacrylic acid and polyethylene oxide.

In a less preferred embodiment said polyethylene oxide is esterified on one end with (meth)acrylic acid and bears a hydroxy group on the other end.

In a preferred embodiment said polyethylene oxide is esterified on one end with (meth)acrylic acid and has been functionalized on the other end, for example by pro forma etherification with an alkyl group like methyl, ethyl, propyl or butyl, preferably methyl. The latter are normally obtained by alkoxylation of alcohols like methanol.

Thus, in one embodiment, ester E is an ester of acrylic acid and polyethylene glycol mono alkyl ether. In one embodiment, ester E is an ester of methacrylic acid and polyethylene glycol mono alkyl ether.

Polyethylene oxide in this context shall mean a polyalkylene oxide that consists essentially of oxyethylene units and optionally a terminal alkyl ether group. In particular, polyethylene oxide comprises less than 10 mol % of oxyalkylene units different from oxyethylene. Preferably, polyethylene oxide as used in this context comprises less than 5 mol %, more preferably less than 1 mol % of oxyalkylene units different from oxyethylene. In an especially preferred embodiment polyethylene oxide as used herein consists of oxyethylene units and a terminal alkyl ether group. Polyethylene oxide is in many cases prepared by ring opening polymerization of ethylene oxide using alcohols like methanol, ethanol, n/iso-propanol or n/sec/tert-butanol as a starter.

Preferably, ester E has an average molar mass Mn of 300 to 10.000 g/mol, more preferably 500 to 10,000 and even more preferably 800 to 10,000 g/mol, especially preferably 1,000 to 10,000 g/mol and particularly preferably 1500 to 10,000 g/mol.

In another embodiment, ester E has an average molar mass Mn of 300 to 8,000 g/mol, more preferably 300 to 5,000 and even more preferably 300 to 3,000 g/mol and especially preferably 300 to 2000 g/mol.

In especially preferred embodiments, ester E has an average molar mass Mn of 500 to 8000 g/mol, 1000 to 5000 g/mol, 800 to 3000 g/mol, 1000 to 3000 g/mol, 800 to 2500 g/mol or 1500 to 2000 g/mol.

In one embodiment, polymer P is a copolymer of styrene and ester E and comprises up to 10% by weight of monomers different from styrene and ester E, preferably up to 5% and more preferably up to 1% by weight. In one embodiment, polymer P consists essentially of or consists of styrene and ester E.

Polymer P has usually a number average molar mass Mn of 5,000 to 100,000 g/mol, preferably of 5,000 to 80,000, and in particular of 10,000 to 50,000. Polymer P has usually a weight average molar mass Mw of 10,000 to 300,000 g/mol, preferably of 20,000 to 150,000, and in particular of 30,000 to 80,000. All values for the average molar mass Mn or Mw given in this application may be determined by gel permeation chromatography (GPC), e.g. using the method as described in the experimental section of this application.

Polymer P is normally prepared by radical polymerization of monomer M, especially styrene, and ester E.

In one preferred embodiment, polymer P is prepared by solution polymerization. "Solution polymerization" means that all starting materials are at least partly dissolved in the same solvent and that the polymerization reaction takes place in homogenous phase, without additional surfactants having to be present. In one preferred embodiment, Monomer M, especially styrene, and ester E are dissolved in suitable solvents like alcohols like methanol, ethanol, 1-propanol, 2-propanol, butanol or mixtures thereof and are then polymerized. Preferably, such solvents for the solution polymerization of Monomer M, especially styrene, and ester E comprise at least 50% by weight, preferably 70% and more preferably 80% by weight of alcohols like methanol, ethanol, 1-propanol, 2-propanol, butanol or mixtures thereof. Preferably, such solvents for the solution polymerization of styrene and ester E comprise 20% by weight or less, preferably 10% by weight or less of water. Unpolar solvents like hydrocarbons (for example aromatic solvents like toluene) are in principle also possible solvents for such solution polymerizations. However, they yield polymers with different properties. In particular, the antifouling properties of such polymers are not as beneficial as from alcohols. Thus, it is preferred to have such hydrocarbons like toluene present in the polymerization solvent in amounts of 20% by weight and below, preferably of 10% by weight and below based on the solvent mixture.

Said radical polymerization can in one embodiment be initiated by oxidative radical starters like organic peroxides (e.g. sodium persulfate, potassium persulfate, metachloroperbenzoic acid). In another embodiment, radical polymerization is initiated by azo starters like azo-bisisobutyrodinitrile or 2,2'-Azobis(2-methylbutyronitrile) (V-59, Wako pure chemical industries, Ltd).

Polymers P obtained by solution polymerization yield aqueous solutions that are very effective with respect to the reduction of fouling. In many cases, Polymers P obtained by solution polymerization yield aqueous solutions that are clear and do not show any turbidity at room temperature.

In one embodiment, polymer P is prepared by emulsion polymerization.

Polymer P is preferably a statistical copolymer in which monomer M, especially styrene, and ester E are distributed statistically.

According to the invention, surface O is usually at least partly coated with at least one polymer P. The term "coated" shall mean that polymer P has been deposited on surface O, covering it at least partly. Polymer P is normally bound to surface O via physisorption like adhesion.

In one embodiment, the surface O comprises a self-assembled monolayer of at least one polymer P. A "self-assembled monolayer" means a molecular assembly formed spontaneously on a surface by adsorption and organized into large (relative to the thickness of the layer) ordered domains. Self-assembled monolayers normally have a thickness that correlates with the size of the individual molecules adsorbed to that surface and that is normally smaller than 100 nm. Such self-assembled monolayers form spontaneously on such surfaces without any further process step being required. After formation of a monolayer, the supernatant solution can be removed as a whole, for example by wiping or using a pipette or by exchanging the polymer solution with a solvent that does not comprise of the polymer. Self-assembled monolayers can for example be characterized by atomic force microscopy (AFM) or X-ray photoelectron spectroscopy (XPS) or in situ methods such as quartz crystal microbalance or surface plasmon resonance spectroscopy.

In one embodiment, especially when polymer P is applied to the surface O of device D as a "self-assembled monolayer", polymer P is comprised on the surface O of device D where polymer P has been applied in amounts of 100 to 2000 $ng/cm^2$.

In another embodiment, the surface O comprises a multilayer of polymer P. The latter can for example be obtained by a "forced" deposition. A forced deposition is a method wherein Polymer P is applied from a solution and subsequently the solution is not withdrawn as a whole, but only the solvent is removed, for example by evaporation, leaving the formerly dissolved polymer P deposited on surface O. A forced deposition can be applied by filling wells of a plate with the solution of polymer P followed by drying, alternatively, a forced deposition can be applied by dip coating, spin-coating, spraying, draw-down bar application, and other methods.

Typically, when polymer P is applied to the surface O of device D by forced deposition, polymer P is comprised on the surface O of device D where polymer P has been applied in amounts larger than 2000 $ng/cm^2$. For example, the surface area of one well of a standard 24 well plate is approximately 2 $cm^2$. If 300 µL of a solution comprising 0.1% of polymer P are applied to such a well and the solvent removed by evaporation, the deposited amount of polymer P is approximately 150 $µg/cm^2$.

Another aspect of the present invention are processes for making devices D, wherein a solution S of at least one polymer P is applied to the surface O. Optionally, the solvent of solution S is removed after applying solution S on said surface.

In another form the invention relates to a process for making the device D comprising the following steps:
A) Providing the device D suitable for cultivating cell cultures having the surface O, and
B) Applying a solution S of at least one polymer P in a solvent L, wherein the polymer P is a copolymer of at least one monomer M and at least one ester E of (meth)acrylic acid and polyethylene oxide, wherein the monomer M is different from ester E and has at least one ethylenically unsaturated double bond.

In another form processes for making devices D preferably comprise the following steps:
A) Providing a device suitable for cultivating cell cultures having a surface O, and
B) Applying a solution S of at least one polymer P in a solvent L, wherein said polymer P is a copolymer of at least one monomer M and at least one ester E of (meth)acrylic acid and polyethylene oxide, wherein said monomer M is different from ester E and has at least one ethylenically unsaturated double bond, wherein polymer P has a surface adsorption SA of at least 200 $ng/cm^2$ on the respective surface where polymer P is deposited, said SA being determined by quartz crystal microbalance.

In another form processes for making devices D preferably comprise the following steps:
A) Providing a device suitable for cultivating cell cultures having a surface O, and
B) Applying a solution S of at least one polymer P in a solvent L, wherein said polymer P is a copolymer of at least one monomer M and at least one ester E of (meth)acrylic acid and polyethylene oxide, wherein said monomer M is different from ester E and has at least one ethylenically unsaturated double bond, wherein polymer P has a surface adsorption SA of at least 200 $ng/cm^2$ on polystyrene.

Upon the application of solution S to surface O, polymer P will normally self-organize to form a layer, in many cases a monolayer, of polymer P on surface O. Thus, for making devices D it will in many cases be sufficient to apply solution S to surface O and wait for a short period of time, for example 1 minute to 1 day, preferably 5 minutes to 2 hours. Once a layer of polymer P has been formed on surface O, the residual solution S can be removed, for example mechanically (for example by wiping or using a pipette) or by exchanging solution S by water or an (aqueous) solution that does not comprise of polymer P.

In one embodiment, processes for making devices D preferably comprise the following steps:
A) Providing a device suitable for cultivating cell cultures having a surface O,
B) Applying a solution S of at least one polymer P, wherein said polymer P is a copolymer of at least one monomer M and at least one ester E of (meth)acrylic acid and polyethylene oxide, wherein said monomer M is different from ester E and has at least one ethylenically unsaturated double bond (preferably wherein polymer P has a surface adsorption SA of at least 200 $ng/cm^2$ on polystyrene), and
C) Removing the supernatant solution S.

In one embodiment, processes for making devices D comprise the following steps:
A) Providing a device suitable for cultivating cell cultures having a surface O, and
B) Applying a solution S of at least one polymer P comprising monomer M, especially styrene, and at least one ester E of (meth)acrylic acid and polyethylene oxide in a molar ratio of 0.05:1 to 50:1.

In one embodiment, processes for making devices D comprise the following steps:
A) Providing a device suitable for cultivating cell cultures having a surface O,
B) Applying a solution S of at least one polymer P comprising monomer M, especially styrene, and at least one ester E of (meth)acrylic acid and polyethylene oxide in a molar ratio of 0.05:1 to 50:1, and C) Removing the supernatant solution S.

In one preferred embodiment, processes for making devices D comprise the following steps:
A) Providing a device suitable for cultivating cell cultures having a surface O,
B) Applying a solution S of at least one polymer P comprising monomer M, especially styrene, and at least one ester E of (meth)acrylic acid and polyethylene oxide in a molar ratio of 0.05:1 to 50:1, and
C1) Removing the solution S, or alternatively
C2) Exchanging solution S for a solution or for a pure solvent or solvent mixture that does not contain polymer P, for example a cell culture medium or water such that a self-assembled (mono)layer of polymer P is deposited on surface O.

Alternatively, the solvent L of solution S can be removed, for example by simple evaporation, such that an additional multilayer of polymer P is deposited on surface O.

In another preferred embodiment, processes for making devices D comprise the following steps:
A) Providing a device suitable for cultivating cell cultures having a surface O,
B) Applying a solution S comprising at least one polymer P and a solvent L to surface O of said device, and
C) Removing the solvent L (thus usually generating a coating of said at least one polymer P on surface O).

Said aqueous solution S normally comprises 0.001 to 10% by weight of polymer P based on the solution S, preferably 0.01 to 1% by weight and even more preferably 0.05 to 0.3% by weight.

In a preferred embodiment, solution S is an aqueous solution. "Aqueous" in this context shall mean that said polymer P is dissolved in a solvent or solvent mixture that comprises at least 50% by weight, preferably at least 70% by weight, more preferably at least 90% by weight and particularly preferably at least 99% by weight of water. In a preferred embodiment, the solvent in which said at least one polymer P is dissolved is water.

An "aqueous solution" of at least one polymer P shall mean that said at least one polymer P is completely or partly dissolved in an aqueous solvent. In a preferred embodiment, said aqueous solution S is a clear solution without any turbidity. In another embodiment, said aqueous solution S comprises polymer P at least partly in dissolved state but shows turbidity. Preferably, solution S is an aqueous solution comprising at least 50% of water.

In another embodiment, solution S comprises at least 50% by weight, preferably at least 70% by weight, more preferably at least 90% by weight and particularly preferably at least 99% by weight of at least one alcohol like methanol, ethanol, n/iso-propanol or n/sec/iso/tert-butanol.

Through the deposition of polymer P on surface O, the properties of device D are improved such that they allow improved cultivation of cells therein.

In one embodiment, devices D comprising at least one polymer P are subjected to a sterilization prior to their application for cultivating cell cultures C.

In one preferred embodiment sterilization of devices D is carried out by exposing devices D comprising at least one polymer P to ethyleneoxide, preferably to gaseous ethyleneoxide.

In case devices D are subjected to sterilization, for example using ETO, it is preferred to have polymer P deposited on surface O as a multilayer in amounts larger than 2000 ng/cm$^2$.

Another aspect of the invention are devices D prepared by processes according to the invention for making devices D.

Another aspect of the present invention is the use of the device D for cultivating cell cultures C.

In one embodiment, cell cultures C are adherent cell cultures.

In one embodiment, cell cultures C are non-adherent cull cultures. In one embodiment, devices D are used for cultivating cell cultures C as non-adherent cell cultures. In particular, devices D can be used for cultivating cell Cultures C that normally grow as adherent cell cultures or cell cultures C that can be cultivated as adherent or as non-adherent cell cultures as non-adherent cell cultures. The term "non-adherent cell culture" is familiar to the skilled person and means that in such cell cultures cells are grown in a cell-suspension without attaching to a surface of the cell culture device.

In one embodiment cell cultures C are embryonal stem cells.

In one embodiment cell cultures C are selected from multicellular eukariotes, especially plant, animal or human derived cells, induced pluripotent cells, stem cells and progenitor cells (with exception of embryonal stem cells), blood cells, especially human blood cells, cells derived from human or animal organs like mammary gland, colon, liver, kidney, pancreas, prostate lung, stomach or brain cells that can be cultivated as organoid cultures as well as cancer cells related to such organs.

In one especially preferred embodiment, cell cultures C are cancer cells, especially human cancer cells like breast cancer cells or prostate cancer cells.

For example for embryonal stem cells or for pluripotent cells, it is advantageous to use devices D for cultivating such cell cultures as non-adherent cell cultures. Thereby such embryonal stem cells or pluripotent cells can grow while keeping their potency but avoiding differentiation into more specialized cells.

Another aspect of the present invention is the use of the polymer P, wherein said polymer P is a copolymer of at least one monomer M and at least one ester E of (meth)acrylic acid and polyethylene oxide, wherein said monomer M is different from ester E and has at least one ethylenically unsaturated double bond, for providing a device for cultivating cell cultures C.

Another aspect of the present invention is the use of polymers P, wherein said polymer P is a copolymer of at least one monomer M and at least one ester E of (meth) acrylic acid and polyethylene oxide, wherein said monomer M is different from ester E and has at least one ethylenically unsaturated double bond, wherein polymer P has a surface adsorption SA of at least 200 ng/cm$^2$ on the respective surface where polymer P is deposited, for providing a device for cultivating cell cultures C.

Another aspect of the present invention is a process for cultivating cell cultures C, comprising the following steps:
a) Providing the device D suitable for cultivating cell cultures, and
b) Cultivating cell cultures C in the supernatant medium above the surface of the device D.

Another aspect of the present invention are processes for cultivating cell cultures C, comprising the following steps:
a) Providing a device D suitable for cultivating cell cultures wherein said device D has a surface O and comprises on its surface O at least one polymer P wherein said polymer P is a copolymer of at least one monomer M and at least one ester E of (meth)acrylic acid and polyethylene oxide, wherein said monomer M is different from ester E and has at least one ethylenically unsaturated double bond (preferably wherein polymer P has a surface adsorption SA of at least 200 ng/cm² on the respective surface where polymer P is deposited, said SA being determined by quartz crystal microbalance), and b) Cultivating cell cultures C in the supernatant medium above the surface of said device D.

In one embodiment, device D is prepared in situ by providing a device suitable for cultivating cell cultures and applying a cell culture cultivation medium comprising 0.001 to 30% by weight, preferably 0.01 to 3% by weight and even more preferably 0.05 to 1% by weight of at least one polymer P based on the medium. It is assumed that through this process a device D is prepared in situ that allows for efficient cultivation of such cell cultures.

In a preferred embodiment, processes for cultivating cell cultures according to the invention are used for cultivating non-adherent cell cultures.

The invention has various advantages:

Devices D are suitable for cultivating cell cultures, especially as non-adherent cell cultures.

Devices D show improved anti-adhesive behavior. Devices D are easy to clean.

Devices D can be used many times. Devices D are easy and economical to make.

Devices D allow for the growing of cell cultures with a high circularity (meaning a round cell morphology). The circularity is a parameter defining how spherical (round) an object is. It is calculated by 4*PI*cell area/square of cell perimeter.

Devices D allow for the growing of non-adherent cell cultures with a very low degree of adhesion to the surface of said device D.

Devices D allow for the growing of non-adherent cell cultures with a round cell morphology.

Devices D allow for the growing of cell cultures that are essentially free floating in the medium and can be easily harvested.

Devices D allow for the cultivation of embryonal stem cells or of pluripotent cells while avoiding a premature specialization of such cells.

EXAMPLES

Abbreviations Used

SA Surface Adsorption
PEGMA polyethylene glycol methacrylic ester
PEGMA2000 polyethylene glycol methacrylic ester with an average molecular mass Mn of 2000 g/mol
FBS fetal bovine serum
Mn average molecular weight
QCM quartz crystal microbalance
PES polyethersulfone
PVDF polyvinylidene difluoride
PA polyamide
PS polystyrene
HEPES 4-(2-hydroxyethyl)-1-piperazineethanesulfonic acid
h hour(s)
s second(s)
"Corning@ Costar® 24 Well ultralow low attachment multiple well plates" comprise a covalently bound hydrophilic, non-ionic, neutrally charged hydrogel.

"Corning@ Costar® 24 Well, untreated" are clear, not treated multiple well plates (Corning Product No. Product #3738).

Molecular weights Mn or Mw were determined by gel permeation chromatography (Size Exclusion Chromatography) as follows: Size Exclusion Chromatography was completed using a mixed bed scouting column for water soluble linear polymers, TSKgel GMPWxl from Tosoh Bioscience LLC, at 35° C. The eluent used was 0.01 M phosphate buffer at pH=7.4 containing 0.01 M sodium azide. The polymer used as 1.5 mg/mL concentrated solution in the eluent. Before injection in a 100 μL injection loop, all samples were filtered through a Millipore IC Millex-LG (0.2 μm) filter. The calibration was carried out with narrow poly(ethylene glycol) samples from PL having molecular weights between 106 and 1,378,000 g/mol. Values outside this interval were extrapolated. For Mn and Mw calculations 3800 g/mol was fixed as the lower limit.

The SA was determined by The Quartz-Crystal Microbalance with dissipation monitoring (QCM-D, a special embodiment of the QCM method). The Quartz-Crystal Microbalance with dissipation monitoring (QCM-D) measures the resonance frequency of a freely oscillating quartz crystal after excitation. The shift in resonance frequency scales inversely proportionally with mass changes at the quartz surface. The SA was calculated from the shift of the $7^{th}$ overtone of the resonance frequency according to the method of Sauerbrey (G. Sauerbrey, Zeitschrift für Physik 1959, volume 155, pages 206-222). The Q-Sense E4 (Biolin Scientific Holding AB) operating system has a mass sensitivity of about 2 ng/cm². QCM measurements were performed using standard flow-through methods with a flow rate of 50 μL/min at 23° C. An experiment comprised the following steps: 1) 10 mmol/L HEPES buffer pH 7 (="buffer") until a stable baseline was achieved; 2) 2 h 0.1 wt % polymer solution in buffer; 3) 2 h buffer; 4) optionally 0.5 h 0.1 wt % BSA or milk in buffer pH 7 for determining the BSA or milk adsorption; 5) 0.5 h buffer.

For cases in which the SA of polymer P on a surface different from quartz was to be determined, model polymer surfaces were generated on the QCM sensor surface by coating with a layer with a thickness of 10 to 500 nm (determined through the weight difference of the QCM sensor) of the respective model polymer. The thickness of the model polymer layer does not affect the results of the QCM measurement as long as it is within the specified range. Means for generating a model polymer layer on a quartz surface are known to skilled persons. Methods for generating model polymer layers on the QCM sensor include dip-coating (for example for PES and PVDF) and spin-coating (for example for PS and TOPAS®). For dip-coating, the sensor was briefly immersed into a 1% solution of the respective polymer in N-methyl-pyrrolidone and subsequently dried at 200° C. using a heat gun. Dip coating was applied to facilitate the removal of the high boiling solvent NMP. For spin-coating, a 40 μL drop of 1% polymer solution in tetrahydrofuran (PS) or xylene (TOPAS) was placed in the center of the quartz crystal and spread across the surface by spinning at 4000 rpm for 30 s. The method for generating the model polymer surface can be chosen by the skilled person based on the boiling point of the solvent in which the model surface polymer is dissolved provided that complete coverage of the surface is achieved. Polystyrene surfaces are coated by spin coating. Polyethersulfone surfaces are coated by dip-coating.

When no other solvent is given in the experimental procedure, such experiments were carried out in water.

The adhesion and spreading behavior of two cell lines, namely MCF-7 (human breast cancer cell line derived from adenocarcinoma, Deutsche Sammlung von Mikroorganismen und Zellkulturen, Braunschweig, Germany) and mouse L929 Fibroblasts (*European Collection of Cell Cultures*, #85011425) cells (in the following, cell lines) on different polystyrene-based 24 multiwell plates have been analyzed.

Example 1: Preparation of Copolymer P1

300 parts by weight of isopropanol and 400 parts by weight of PEGMA2000 50 wt % solution in water were mixed under nitrogen and heated to 75° C. Once the inner temperature had reached 70° C., 0.4 parts by weight of 2,2'-azobis(2-methylbutyronitrile) (Wako V 59, Wako Chemicals GmbH, Germany) dissolved in 20 parts by weight of isopropanol were added and the mixture was heated to 75° C. for one hour. Afterwards, 10.4 parts by weight of styrene in 80 parts by weight of isopropanol and 2 parts by weight of Wako V 59 in 100 parts by weight of isopropanol were added within the next 2 hours. Thereafter, 2 parts by weight of Wako V 59 in 100 parts by weight of isopropanol were added during 6 h. The total reaction mixture was kept at 75° C. for another 2 hours, before being submitted to purification by water steam distillation. The Copolymer P1 had a Mn of 23,000 g/mol and a Mw of 54,380 g/mol.

Example 2: Surface Adhesion SA of Copolymer P1 Determined by QCM

The SA of polymer coatings on the model surface and protein adsorption were determined by QCM-D by the method given above.

Adsorption of polymer on the model surfaces was carried out by equilibrating the modified quartz sensor surface with 0.1 wt % polymer solution in HEPES buffer until a monolayer was formed (step 2) above). Afterwards, the sensor surface was rinsed with buffer until a stable mass reading was obtained (step 3) above).

Protein adsorption was monitored during exposure of the samples to 0.1 wt % solution of milk powder in HEPES buffer for 0.5 h. The final mass change was recorded after another 0.5 h of rinsing with buffer (steps 4) and 5) above).

Example 2.1: Surface Adhesion SA of Polymer P1 on Polystyrene=1045+/−107 ng/cm². Milk Adsorbed Amount=0+/−1 ng/cm²

Example 3: Functionalization of Non-Treated Polystyrene with Polymer P1

All subsequent steps were carried out in a sterile bench: Non-treated multiwell plates made of polystyrene (Corning® Costar® 24 Well, untreated) were pre-treated with a solution of 0.1% Polymer P1 in deionized water (500 µL for each well) (Milli-Q@, Merck Millipore) for 1 hour at room temperature and subsequently rinsed three times with deionized water and then dried at room temperature for 12 hours. The product was stable and could be stored for several weeks.

Example 4: Functionalization of Non-Treated Polystyrene with Polymer P1 (Forced Deposition)

All subsequent steps were carried out in a sterile bench: Non-treated multiwell plates made of polystyrene (Corning® Costar® 24 Well. untreated) were coated with the following procedure: 300 µL of 0.1% polymer P1 solution in deionized water (Milli-Q®, Merck Millipore) were transferred into each well of the 24 well plate. Subsequently, the water was allowed to evaporate statically under a sterile bench for 24 hours at room temperature. Afterwards, the product is stable and can be stored for several weeks.

Example 5: Cell Culture

Conditions were as Follows for Fibroblasts L929:
1). non-treated polystyrene (Corning® Costar® 24 Well, untreated) (control), (C1),
2). low-adhesion plates based on covalently bound hydrophilic, non-ionic, neutrally charged hydrogel (Corning® Costar® 24 Well Ultra-Low Attachment Multiple Well Plates) (C2),
3). non-treated polystyrene (Corning® Costar® 24 Well, untreated) multiwell plates that have been pre-coated with polymer P1 using the procedure described in Example 3. Prior to cell culture experiments, the polymer-coated well-plates were rehydrated in deionized water for 1 hour. (C3),
4). non-treated polystyrene (Corning® Costar® 24 Well, untreated) multiwell plates that have been pre-coated with polymer P1 using the procedure described in Example 4. Prior to cell culture experiments, the polymer-coated well-plates were rehydrated in deionized water for 1 hour. (C4),
5) non-treated polystyrene (Corning® Costar® 24 Well, untreated) multiwell plates that have been pre-coated with polymer P1 using the procedure described in Example 4 and subsequently treated with ETO (ethylene oxide) for sterilization (ETO-sterilization was done according to EN ISO 11135:2007& 2014 Sterilization of Healthcare products, EN ISO 9001:2008 Quality Management System and ISO 13485:2012 Quality System—Medical Devices, NL27S11829771-2-1). After sterilization, the samples can be stored for several months. Prior to cell culture experiments, the polymer-coated well-plates were rehydrated in deionized water for 1 hour. (C5).

Conditions were as Follows for MCF-7:
6) non-treated polystyrene (Corning® Costar® 24 Well, untreated) (control), (C6),
7) low-adhesion plates (Corning® Costar® 24 Well Ultra-Low Attachment Multiple Well Plates), (C7),
8) non-treated polystyrene (Corning® Costar® 24 Well, untreated) multiwell plates that have been pre-coated with polymer P1 using the procedure described in Example 3. Prior to cell culture experiments, the polymer-coated well-plates were rehydrated in deionized water for 1 hour. (C8).

MCF-7 cells were cultured in RPMI (Roswell Park Memorial Institute) 1640 medium (sourced from PanBiotech, # P04-18500) supplemented with 10%-fetal bovine serum (Biochrom KG, # S 0115), 1× non-essential amino acids (0.75 g/L glycine, 0.89 g/L L-alanine, 1.32 g/L L-asparagine, 1.33 g/L L-aspartic acid, 1.47 g/L L-glutamic acid, 1.15 g/L L-proline, 1.05 g/L L-serine), 1 mM sodium pyruvate, 0.1% human insulin and 1% penicillin/streptomycin.

Fibroblasts L929 cells are mouse fibroblasts derived from an immortalized mouse fibroblast cell line and were cultured in RPMI 1640, PanBiotech (# P04-18500) with stable glutamine/2.0 g/L NaHCO$_3$, 10% FBS (Biochrom KG, # S 0115), supplemented with 1% penicillin/streptomycin (Sigma-Aldrich, # P4333). Semi-confluent cultures were sub-cultured and splitted at approximately 0.5-2×10⁴ cells/cm². Confluent cells were trypsinized using a 0.5% trypsin solution, with EDTA (Sigma-Aldrich, # T3924), and further grown at 37° C. and 5% $CO_2$.

The fibroblast cell line was seeded at a concentration of 74,560 cells/mL on the different 24 multiwell-plates (at conditions 1-5). Quantification was done after 5 days of culture.

The MCF-7 cells were seeded at a concentration of 10,000 cells/mL on the different 24 multiwell-plates (conditions 6-8). The cell lines were supplemented with fresh medium every two days. Quantification was done after 6 days of culture.

The ability of the polymer coating prepared according to the above given conditions to prevent cell adhesion was analyzed by cultivating the before mentioned cell lines in a 24 well plate under the before mentioned 8 different conditions. The cell behavior was characterized using light microscopy (Olympus IX 73, Germany) with a 10× objective. Specifically, the percentage of non-adherent cells was determined after 5 days (L929, examples 5.1-5.5) or 6 days (MCF-7, examples 5.6-5.8) of culture via a shaking test based on the quantification of non-adherent and adherent cells as follows: First, the total number of objects at a field of view with a 10× objective was visually counted (Objects are defined as single cells or cell clusters, see FIG. 1 or 2). Afterwards the well plate was tapped manually multiple times to force a lateral movement of the cell culture medium and all free-floating objects were manually counted. The ratio of free-floating (i.e. non-adherent) objects to the total number of objects was used to calculate the percentage of non-adherent cells as follows:

percentage non-adherent cells=number of free-floating objects/total number of objects*100.   Equation 1

Mean and error of the mean of 10 independent experiments (with 4 different fields of view per sample) have been analyzed. The level of significance was assessed using the student's t-test and all data is significantly different with a confidence of <0.05 if marked with (*).

Results:

L929 Fibroblast Cell Line (Examples 5.1-5.5, Conditions C1-C5):

FIG. 1 shows L929 Fibroblasts after 5 days of culture, conditions C1 to C5 (examples 5.1-5.5). Scale bar: 200 µm. The fibroblasts adhered and spread on the non-treated polystyrene (Comparative example condition C1), the percentage of non-adherent cells was 1.8±1.6% (see FIG. 1 C1 and Table 1). Comparative example, condition C2, showed a low adhesion of fibroblasts with 82.2±12.5% of non-adherent cells. Surprisingly, conditions C3, C4 and C5 showed an even significantly improved anti-adhesive performance as determined by the higher percentage of non-adherent cells with 92.7±6.6%, 96.3±3% and 97±3%, respectively.

Examples 5.1-5.5, Conditions C1-C5, L929 Fibroblasts

TABLE 1

Quantification of non-adherent L929 fibroblasts at the different conditions from C1 to C5, percentage of non-adherent cells was analyzed after 5 days of culture. The level of significance was assessed using a pairwise student's t-test between conditions C3-C5 compared to condition C2. Data is statistically significant with a confidence of <0.05 if marked with (**). Accordingly, significant differences in the percentages of non-adherent cells were observed for conditions C3, C4 and C5 compared to condition C2.

| Example | Condition | Short description | % non-adherent cells/ significance | % Mean error |
|---|---|---|---|---|
| Comparative Example 5.1 | Condition C1 | PS untreated | 1.8 | 1.6 |
| Comparative Example 5.2 | Condition C2 | Corning ® Costar ® 24 Well, Ultra-Low Attachment | 82.2 | 12.5 |
| Example 5.3 | Condition C3 | Polymer P1 0.1% (adsorbed) | 92.7 (**) | 6.6 |
| Example 5.4 | Condition C4 | Polymer P1 0.1% (forced deposition) | 96.3 (**) | 3 |
| Example 5.5 | Condition C5 | Polymer P1 0.1% forced deposition), ETO-treated | 97 (**) | 3 |

Figure 2:
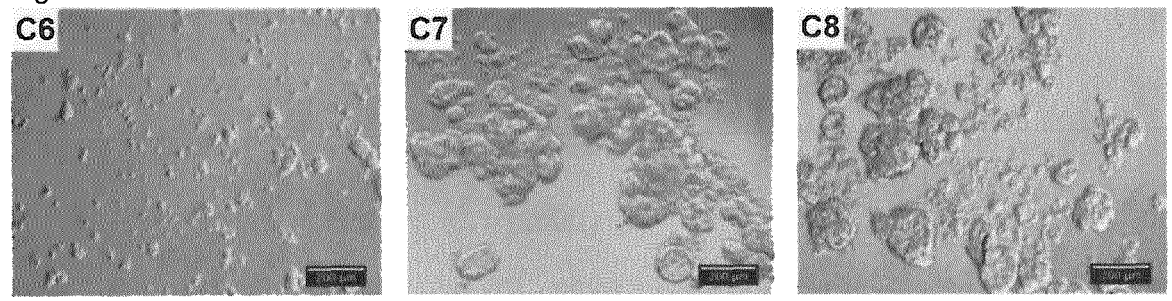

MCF-7 Cell Line (Examples 5.6-5.8, Conditions C6-C8):

FIG. 2 shows MCF-7 cells_after 6 days of culture on conditions C6 to C8 (Examples 5.6-5.8). Scale bar: 200 µm. MCF-7 cells strongly adhere to non-treated polystyrene surfaces (PS control) and show a spread cell-morphology (FIG. 2, comparative example condition C6. The Ultra-Low Attachment surface, comparative example condition C7, showed a high number of free floating cells with 79.7±11% of non-adherent cells (see Table 2). Surprisingly, example condition C8 showed an even significantly higher number of free-floating cells as seen by the percentage of non-adherent cells (93.3±5.3%). MCF-7 cells cultured on condition C8 mainly show big spherically shaped cell aggregates, i.e. the wanted spheroid shape (FIG. 2, condition C8).

Examples 5.6-5.8, Conditions C6-C8, MCF-7 Cell Line

TABLE 2

Quantification of non-adherent MCF-7 cells at the different conditions from C6 to C8. The percentage of non-adherent cells was analyzed after 6 days of culture. The level of significance was assessed using a pairwise student's t-test between conditions C7 and C8. Data is statistically significant with a confidence of <0.05 if marked with (**). Accordingly, significant differences in the percentages of non-adherent cells was observed for condition C8 compared to condition C7.

| Example | Condition | Short description | % non-adherent cells/ significance | % Mean error |
|---|---|---|---|---|
| Comparative Example 5.6 | Condition 6 | PS untreated | 0 | 0 |
| Comparative Example 5.7 | Condition 7 | Corning ® Costar ® 24 Well, Ultra-Low Attachment | 79.7 | 11 |
| Example 5.8 | Condition 8 | Polymer P1 0.1% (adsorbed) | 93.3(**) | 5.3 |

MAIN CONCLUSIONS

The anti-adhesive polymer pre-coating based on polymer P1 was applied on non-treated PS tissue culture well plates. The coatings showed a significantly improved anti-adhesive performance as it was indicated and proven by the significantly higher number of non-adherent cells found for conditions C3, C4, C5 and C8 and a spherical (non-spreaded) cell morphology of both L929 and MCF-7 cell lines. Moreover, the performance of the anti-adhesive polymer pre-coating remains unaltered by ETO (ethylene oxide)-sterilization procedure, drying and rehydration prior to cell culture.

The invention claimed is:

1. A device D for cultivating non-adherent cell cultures C, wherein said device D has a surface O and comprises on its surface O at least one polymer P,
    wherein said polymer P is a copolymer of styrene and at least one ester E of (meth)acrylic acid and polyethylene oxide;
    wherein the device D comprises free floating non-adherent cells.

2. The device D according to claim 1, wherein said device D is selected from the group consisting of flasks, cell culture dishes, cell culture bottles, cell culture bags, pipette tips, petri dishes, multiwall plates, reactors, tubes, pipettes, and syringes.

3. The device D according to claim 1, wherein the polymer P comprises styrene and the at least one ester E in a molar ratio of 0.3:1 to 10:1.

4. The device D according to claim 1, wherein the polymer P has a surface adsorption SA of at least 200 ng/cm$^2$ on the respective surface where polymer P is deposited, said SA being determined by quartz crystal microbalance.

5. The device D according to claim 1, wherein the at least one ester E has an average molar mass Mn of 300 to 10,000 g/mol.

6. The device D according to claim 1, wherein the polymer P has an average molar mass Mn of 5000 to 100,000 g/mol.

7. The device D according to claim 1, wherein the surface O comprises glass, quartz, silicon, metals, metal oxides or organic polymers.

8. The device D according to claim 1, wherein the surface O comprises fluorinated polyolefins, or partially fluorinated polyolefins.

9. A process for cultivating cell cultures C, comprising:
    a) providing the device D suitable for cultivating cell cultures according to claim 1; and
    b) cultivating non-adherent cell cultures C in the supernatant medium above the surface of the device D.

10. The device D according to claim 1, wherein the polymer P is a statistical copolymer in which styrene and ester E are distributed statistically.

11. The device D according to claim 1, wherein said polymer P has a surface adsorption SA of at least 200 ng/cm$^2$ on the respective surface where polymer P is deposited.

12. The device D according to claim 1, wherein the non-adherent cell cultures C are not attached to the surface O.

* * * * *